United States Patent
Leewood et al.

(10) Patent No.: US 8,128,678 B2
(45) Date of Patent: Mar. 6, 2012

(54) STENT HAVING LESS INVASIVE ENDS AND IMPROVED RADIAL FORCE

(75) Inventors: Alan R. Leewood, Lafayette, IN (US); Shuo Yang, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/060,204

(22) PCT Filed: Sep. 2, 2009

(86) PCT No.: PCT/US2009/004940
§ 371 (c)(1), (2), (4) Date: Mar. 14, 2011

(87) PCT Pub. No.: WO2010/027450
PCT Pub. Date: Mar. 11, 2010

(65) Prior Publication Data
US 2011/0166640 A1    Jul. 7, 2011

Related U.S. Application Data

(60) Provisional application No. 61/093,624, filed on Sep. 2, 2008.

(51) Int. Cl.
*A61F 2/82* (2006.01)
(52) U.S. Cl. ...................................... 623/1.15
(58) Field of Classification Search ......... 623/1.15–1.22
See application file for complete search history.

(56) References Cited

U.S. PATENT DOCUMENTS

| | | | |
|---|---|---|---|
| 5,593,442 A | 1/1997 | Klein | |
| 5,728,131 A | 3/1998 | Frantzen et al. | |
| 5,800,456 A | 9/1998 | Maeda et al. | |
| 6,053,940 A * | 4/2000 | Wijay | 623/1.15 |
| 6,251,134 B1 * | 6/2001 | Alt et al. | 623/1.16 |
| 6,312,460 B2 | 11/2001 | Drasler et al. | |
| 6,375,675 B2 | 4/2002 | Dehdashtian et al. | |
| 6,395,020 B1 | 5/2002 | Ley et al. | |
| 6,423,090 B1 * | 7/2002 | Hancock | 623/1.15 |
| 6,506,211 B1 | 1/2003 | Skubitz et al. | |
| 6,527,799 B2 | 3/2003 | Shanley | |
| 6,585,755 B2 | 7/2003 | Jackson et al. | |
| 6,599,314 B2 | 7/2003 | Mathis | |

(Continued)

OTHER PUBLICATIONS

International Search Report and Written Opinion for PCT/US2009/004940 dated Feb. 2, 2010, 16 pgs.

(Continued)

*Primary Examiner* — Suzette J Gherbi
(74) *Attorney, Agent, or Firm* — Brinks Hofer Gilson & Lione

(57) ABSTRACT

The present invention provides a stent having less invasive ends and improved radial force. In one embodiment, the stent comprises a series of proximal apices disposed at a proximal end of the stent, a series of distal apices disposed at a distal end of the stent, and at least one angled strut segment disposed between the proximal and distal apices of the stent. At least one apex of the stent may comprise multiple curved portions. In one example, the radius of curvature of one of the curved portions is significantly greater, for example, at least 10 times greater, than each of the other radii of curvature of the apex. The curved portion having the significantly greater radius of curvature may be configured to engage a vessel wall in a less invasive manner.

20 Claims, 5 Drawing Sheets

U.S. PATENT DOCUMENTS

| | | |
|---|---|---|
| 6,663,664 B1 | 12/2003 | Pacetti |
| 6,786,922 B2 * | 9/2004 | Schaeffer .................... 623/1.15 |
| 6,790,227 B2 | 9/2004 | Burgermeister |
| 6,805,707 B1 * | 10/2004 | Hong et al. ................. 623/1.16 |
| 6,821,292 B2 * | 11/2004 | Pazienza et al. ............. 623/1.15 |
| 6,846,323 B2 * | 1/2005 | Yip et al. .................... 623/1.16 |
| 7,128,756 B2 | 10/2006 | Lowe et al. |
| 7,335,228 B2 * | 2/2008 | Schaeffer .................... 623/1.15 |
| 7,473,275 B2 * | 1/2009 | Marquez ..................... 623/2.38 |
| 7,842,080 B2 * | 11/2010 | Chouinard .................. 623/1.15 |
| 2004/0093072 A1 | 5/2004 | Pappas et al. |
| 2005/0070991 A1 | 3/2005 | Pienknagura |
| 2005/0090894 A1 * | 4/2005 | Pazienza et al. ............. 623/1.15 |
| 2006/0004436 A1 | 1/2006 | Amarant et al. |
| 2006/0111771 A1 | 5/2006 | Ton et al. |
| 2006/0271164 A1 * | 11/2006 | Shaolian et al. ............. 623/1.16 |
| 2007/0112412 A1 | 5/2007 | Shokoohi et al. |
| 2007/0150048 A1 * | 6/2007 | Tischler ...................... 623/1.16 |
| 2007/0219624 A1 * | 9/2007 | Brown et al. ................. 623/1.15 |
| 2009/0171437 A1 * | 7/2009 | Brocker et al. .............. 623/1.13 |
| 2010/0312326 A1 * | 12/2010 | Chuter et al. ................ 623/1.13 |

OTHER PUBLICATIONS

International Report on Patentability for PCT/US2009/004940 dated Aug. 16, 2010, 10 pgs.

Response to the Written Opinion, including amended pp. 2, 2a and claims, dated May 25, 2010, 8 pgs.

* cited by examiner

STENT HAVING LESS INVASIVE ENDS AND IMPROVED RADIAL FORCE

RELATED APPLICATIONS

The present patent document is a §371 filing based on PCT Application Ser. No. PCT/US2009/004940, filed Sep. 2, 2009 (and published as WO 2010/027450A1 on Mar. 11, 2010), designating the United States and published in English, which claims the benefit of the filing date under 35 U.S.C. §119(e) of Provisional U.S. Patent Application Ser. No. 61/093,624, filed Sep. 2, 2008. All of the foregoing applications are hereby incorporated by reference in their entirety.

TECHNICAL FIELD

The present invention relates generally to apparatus and methods for treating medical conditions, and more specifically, to stents for use in body vessels to treat those medical conditions.

BACKGROUND ART

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

With balloon-expandable stents, the stent may be delivered and deployed using a catheter having proximal and distal ends and one or more balloons disposed on the catheter. The stent may be coupled to the balloon during insertion until the target site is reached, and then deployed by inflating the balloon to expand the stent to bring the stent into engagement with the target site. Alternatively, the stent may be placed separately in the vessel and a subsequent catheter having an expansion portion may then be inserted into the stent to expand the stent at the target site.

Various existing self-expanding and balloon-expandable stent designs and configurations comprise end regions including one or more apices. The apices commonly comprise relatively acute bends or present somewhat pointed surfaces, which may facilitate compression of the stent to a relatively small delivery profile due to the tight bend of the apices. Although having this advantage, in some situations, such relatively acute or pointed apices may be undesirable.

For example, in the case of a suprarenal attachment stent employed during treatment of an abdominal aortic aneurysm, the stent may have one end coupled to a graft material and the other end engage a healthy portion of a vessel wall. If the acute bends of the apices that engage the graft material are too pointed, sharp or otherwise invasive, then it may adversely impact or abrade the graft material, leading to breakdown of, or leakage through, the graft material. Similarly, if the ends of the stent that engage the vessel wall are too pointed, sharp or otherwise invasive, then it may have an adverse effect upon the vessel wall in the expanded state.

Certain existing stents comprise relatively round, or arcuate, proximal and distal apices, as opposed to relatively pointed or acute apices. The provision of such rounded apices at the distal and proximal ends of the stent may be less invasive upon graft material and/or vessel walls. However, such well-rounded stents may provide a relatively low radial force and may not provide an adequate sealing force upon a vessel wall.

The present invention overcomes at least one of the above problems and in particular provides a stent having less invasive ends for use in a medical procedure.

DISCLOSURE OF THE INVENTION

According to a first aspect of the present invention, there is provided a stent for use in a medical procedure, the stent comprising:

at least one apex comprising multiple curved portions, where each of the curved portions comprises a radius of curvature, and where the radius of curvature of one of the curved portions is greater than each of the other radii of curvature of the apex.

Advantageously, such a stent is less invasive upon a vessel wall when deployed, and also yields an increased conformance to the vessel wall. Further, the design of a stent having the multiple curved portions described herein yields a significantly increased radial force upon the vessel wall. Moreover, if used in conjunction with a stent-graft, the significantly large radius of curvature yields an increased suture attachment zone, thereby allowing for the provision of a greater number of sutures and enhanced coupling between the stent and the graft.

According to a second aspect of the present invention, there is provided a stent for use in a medical procedure, the stent comprising:

a series of proximal apices disposed at a proximal end of the stent;

a series of distal apices disposed at a distal end of the stent; and where the first curved portion comprises a convex curvature relative to an interior space of the apex, the second, third and fourth curved portions each comprise a concave curvature relative to the interior space, and the fifth curved portion comprises a convex curvature relative to the interior space; and where the third curved portion is configured to be substantially flush against a vessel wall in a deployed state.

According to a third aspect of the present invention, there is provided a stent having proximal and distal ends, the stent comprising:

a series of proximal apices disposed at a proximal end of the stent;

a series of distal apices disposed at a distal end of the stent; and first and second angled strut segments disposed between each proximal apex and each distal apex, wherein central regions of the first and second angled strut segments comprise a concave curvature, such that each central region is bowed radially inward with respect to a central lumen of the stent in the expanded state, and where the first and second angled strut segments are disposed at an angle of about 70 to 110 degrees relative to each other in an expanded state.

In one embodiment, the stent comprises a series of proximal apices disposed at a proximal end of the stent, a series of distal apices disposed at a distal end of the stent, and at least one angled strut segment disposed between the proximal and distal apices of the stent. At least one apex of the stent may comprise multiple curved portions. In one example, the radius of curvature of one of the curved portions of an individual apex is significantly greater than each of the other radii of curvature of the apex. Accordingly, good conformability can be achieved which makes this stent especially suitable for stent graft sealing purposes. The smaller radii of curvature give the stent larger radial force than conventional designs. For example, the radius of curvature of one curved portion may be at least 10 times greater than all other curved portions. The curved portion having the significantly greater radius of curvature may be configured to engage a vessel wall in a less invasive manner.

The curved portion having the significantly greater radius of curvature may be configured to be substantially flush against a vessel wall in a deployed state.

In one particular embodiment, each apex of the stent comprises five curved portions. A first angled strut segment transitions into the first curved portion of the apex, and the first curved portion transitions into the second, third, fourth and fifth curved portions of the apex, respectively. The fifth curved portion of the apex then transitions into a second angled strut segment. The first and second angled strut segments may be disposed at an angle of about 70 to 110 degrees relative to each other in an expanded state, thereby facilitating radial expansion of the stent.

In this embodiment having five curved portions per apex, the first curved portion comprises a convex curvature relative to an interior space of the apex. Further, the second, third and fourth curved portions each comprise a concave curvature relative to the interior space, and the fifth curved portion comprises a convex curvature relative to the interior space. In this example, the third curved portion may be configured to engage a vessel wall and may comprise the radius of curvature that is significantly greater, e.g., at least 10 times greater, than each of the other radii of curvature of the apex. In one embodiment, the third curved portion is near flat.

At least one of the angled strut segments may be curved. This enables the stent to provide a more uniform sealing pressure across the whole stent. There is a more uniform contact pressure between the stent and the vessel wall including at the apices of the stent.

In one embodiment, a central region of at least one of the first and second angled strut segments may comprise a convex curvature, such that the central region is flared radially outward with respect to a central lumen of the stent in the expanded state. Alternatively, the central region of an angled strut segment may comprise a concave curvature, such that the central region is bowed radially inward with respect to a central lumen of the stent in the expanded state. In a further alternative embodiment, at least one angled strut segment may be substantially straight.

A stent as described may be used alone or in conjunction with a stent-graft. The stent may be coupled to the distal end of a graft and used, for example, as an attachment stent for endovascular graft fixation. Alternatively, the stent may be one component of a stent-graft, in which the stent overlaps with the graft material either internally or externally to the graft material.

Advantageously, a stent designed in accordance with the examples described herein is less invasive upon a vessel wall when deployed, and also yields an increased conformance to the vessel wall. Further, the design of a stent having the multiple curved portions described herein yields a significantly increased radial force upon the vessel wall. Moreover, if used in conjunction with a stent-graft, the significantly large radius of curvature yields an increased suture attachment zone, thereby allowing for the provision of a greater number of sutures and enhanced coupling between the stent and the graft.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
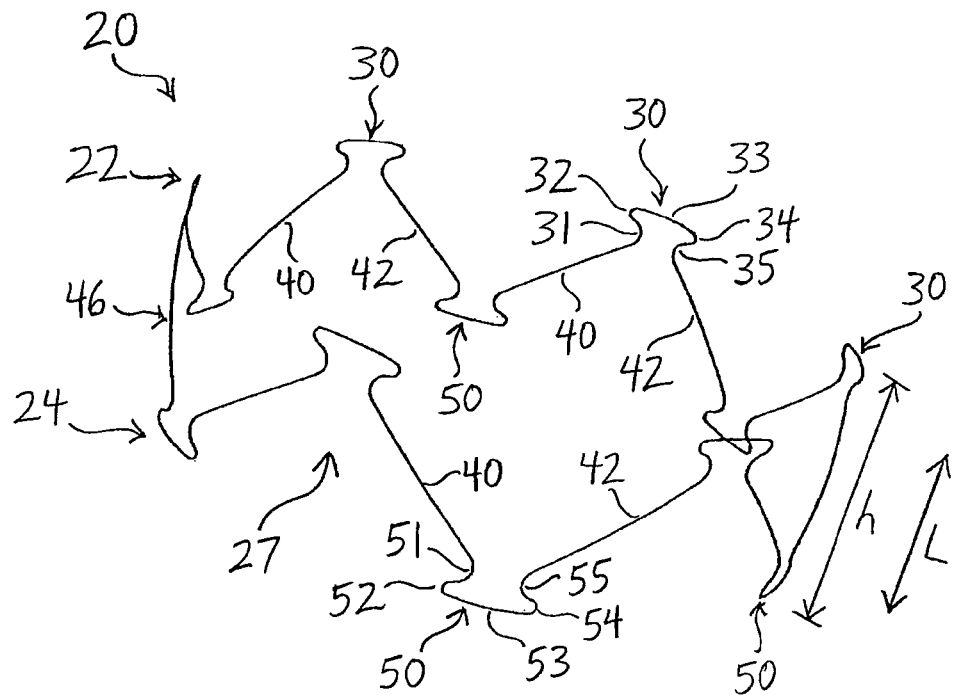
FIG. 1 is a perspective view of a first embodiment of a stent.

Referring now to FIG. 1, a stent 20 provided in accordance with a first example is described. The stent 20 generally comprises a proximal end 22 and a distal end 24. The stent 20 has a reduced diameter delivery state so that it may be advanced to a target location within a vessel or duct. The stent 20 also has an expanded deployed state, shown in FIG. 1, in which the stent 20 is configured to apply a radially outward force upon at least a portion of a vessel or duct, e.g., to maintain patency within a passageway, or to hold open the lumen of a graft. In the expanded state, fluid flow is allowed through a central lumen 27 of the stent 20.

As shown in FIG. 1, the proximal end 22 of the stent 20 may comprise multiple adjacent proximal apices 30, while the distal end 24 of the stent 20 may comprise multiple adjacent distal apices 50. In this embodiment, the apices 30 located at the proximal end 22 are identical to the apices 50 located at the distal end 24. Since the stent is symmetric, it offers a uniform circumferential sealing force across the stent.

The proximal and distal apices 30 and 50 are separated by a series of first and second angled strut segments 40 and 42, respectively. In the expanded state depicted in FIG. 1, each of the first angled strut segments 40 are generally parallel to one another, while each of the second angled strut segments 42 are generally parallel to one another. Further, in the expanded state, the first and second angled strut segments 40 and 42 may be disposed at an angle of about 70 to 110 degrees relative to each other. By contrast, in the compressed state depicted in FIG. 4D below, the first and second angled strut segments 40 and 42 may be compressed such that they are substantially parallel to one another during delivery of the stent 20.

Figure 4A:
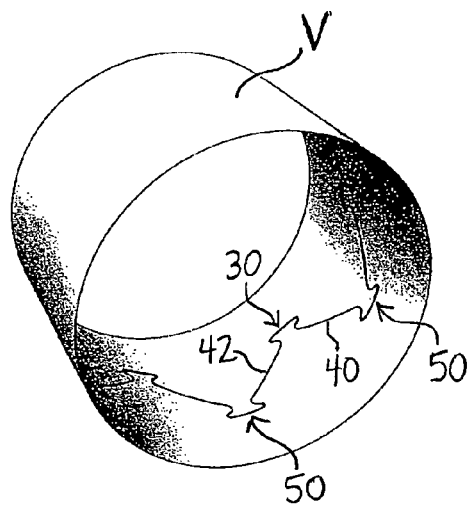
FIGS. 4A-4D are perspective views illustrating the stent of FIG. 1 in four varying degrees of compression.

At least one of the first and second angled strut segments 40 and 42 may comprise a curvature relative to a vessel wall, i.e., along a longitudinal axis L of the stent 20. This enables the stent to provide a more uniform sealing pressure across the whole stent. In the embodiment of FIG. 1, multiple first and second angled strut segments 40 and 42 comprise a convex curvature relative to a vessel wall, in which central regions 46 of the first and second strut angled strut segments 40 and 42 are flared radially outward with respect to the central lumen 27 in the expanded state. Accordingly, the central region 46 imposes an enhanced radial force upon a vessel wall, as depicted in FIG. 4A below.

Alternatively, at least one of the first and second angled strut segments 40 and 42 may comprise a concave curvature relative to a vessel wall, in which the central region 46 is bowed radially inward with respect to the central lumen 27 in the expanded state, as depicted and explained in FIGS. 5-6 below. In the latter embodiment, the proximal and/or distal apices 30 and 50 may be configured to apply an increased forced upon a vessel wall. In yet a further alternative embodiment, the first and second angled strut segments 40 and 42 may be substantially straight, i.e., comprise neither a convex nor concave curvature relative to the vessel wall.

The stent 20 may comprise a single wire having a round or flat cross-sectional profile. If a round cross-sectional profile is employed, the wire diameter of the stent 20 may range from about 0.010 to about 0.020 inches. Moreover, the height h of the stent 20, i.e., the longitudinal distance between an end of a proximal apex 30 and an end of a distal apex 50, as depicted in FIG. 1, may range from about 10.0 to about 20.0 mm.

Figure 2:
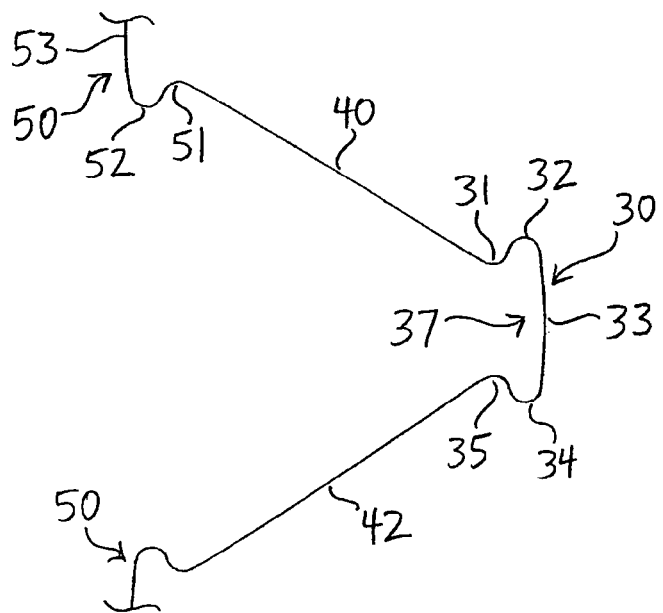
FIG. 2 is a side view illustrating an apex of the stent of FIG. 1.

As shown in FIGS. 1-3, an individual exemplary apex 30 may comprise five curved portions 31-35. An interior space 37 of the apex 30 is depicted for reference purposes. A first curved portion 31 comprises a convex curvature relative to the interior space 37, as best seen in FIG. 2. A second curved portion 32 comprises a concave curvature relative to the interior space 37, and a third curved portion 33 also comprises a concave curvature relative to the interior space 37. A fourth curved portion 34 comprises a concave curvature relative to the interior space 37, in a substantially symmetrical manner to the second curved portion 32, as shown in FIGS. 1-3. Finally, a fifth curved portion 35 comprises a convex curvature relative to the interior space 37, in a substantially symmetrical manner to the first curved portion 31.

As best seen in FIG. 2, one of the first angled strut segments 40 transitions into the first curved portion 31 of the apex 30, which then transitions into the second curved portion 32. The second curved portion 32 transitions into the third curved portion 33, which is effectively the peak of the apex 30. The third curved portion 33 transitions into the fourth curved portion 34 of the apex 30. The fourth curved portion 34 transitions into the fifth curved portion 35, which then transitions into one of the second angled strut segments 42. Subsequently, the second angled strut segment 42 transitions into a curved portion 55 of one of the distal apices 50, as shown in FIGS. 1-2.

In the present example, each distal apex 50 comprises five curved portions 51-55 that are structurally identical to the five curved portions 31-35, respectively, of each proximal apex 30. Accordingly, a cylindrically-shaped stent 20 may be formed having proximal and distal apices 30 and 50 that are structurally identical, and which are separated by the series of first and second angled strut segments 40 and 42, as shown in FIG. 1. It may be noted that the each of the proximal apices 30 are circumferentially offset from the distal apices 50, i.e., when the stent 20 is cylindrically formed, a proximal apex 30 is circumferentially offset from a distal apex 50, which in turn is offset from the next adjacent proximal apex 30, as shown in FIG. 1.

Figure 3A:
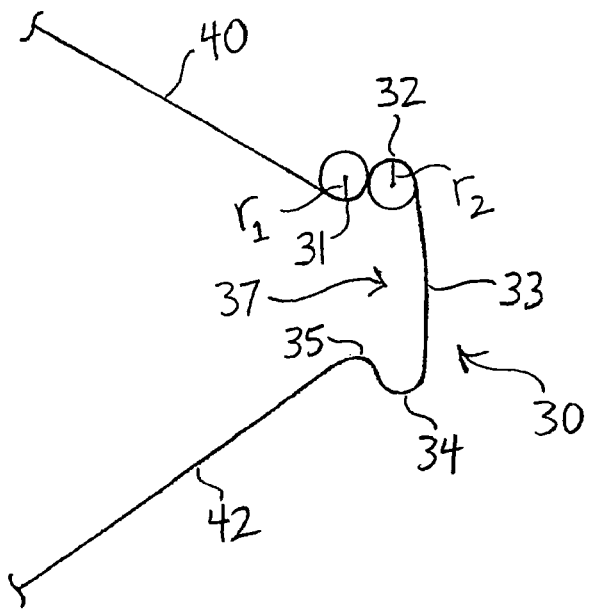
FIGS. 3A-3B are side views illustrating features of an apex of the stent of FIGS. 1-2.
Figure 3B:
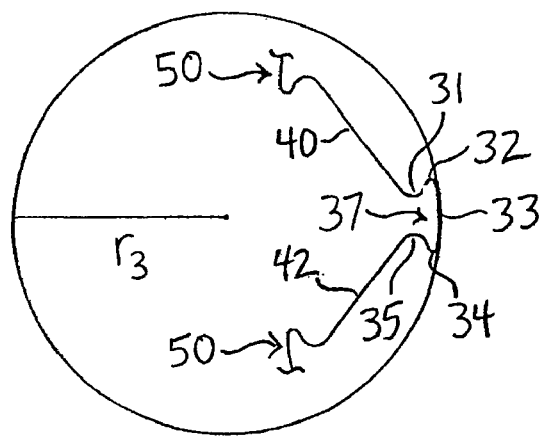

Referring now to FIGS. 3A-3B, further features of an exemplary apex 30 are described. The first curved portion 31 of the apex 30 may comprise a radius of curvature $r_1$, while the second curved portion 32 may comprise a radius of curvature $r_2$, as shown in FIG. 3A. The third curved portion 33 may comprise a radius of curvature $r_3$, as shown in FIG. 3B. Preferably, the fourth curved portion 34 comprises a radius of curvature that is substantially identical to the radius of curvature $r_2$ of the second curved portion 32, while the fifth curved portion 35 comprises a radius of curvature that is substantially identical to the radius of curvature $r_1$ of the first curved portion 31.

As shown in FIGS. 3A-3B, the radius of curvature $r_3$ of the third curved portion 33 is significantly larger than the radii of curvature $r_1$ and $r_2$. Solely by way of example, the radius of curvature $r_3$ may be about 10-60 times greater than the radii of curvature $r_1$ and $r_2$, and more preferably in the range of about 25-40 times greater.

For example, if the stent 20 is configured to be disposed in an aorta to provide a radial sealing force upon the aorta, the radius of curvature $r_3$ of the third curved portion 33 may range from about 10.0-20.0 mm, while the radii of curvature $r_1$ and $r_2$ may range from about 0.3 to about 5.0 mm. Such ranges are provided for illustrative purposes only for an aortic application and are not intended to be limiting. Moreover, if the stent 20 is used in other vessels, it may vary the dimensions of the radii of curvature.

In one embodiment, the radius of curvature $r_1$ may be substantially identical to the radius of curvature $r_2$. Alternatively, the radius of curvature $r_1$ may be greater than the radius of curvature $r_2$, or vice versa. Preferably, the radii of curvature $r_1$ and $r_2$ are within a factor of three of each other, e.g., if the radius of curvature $r_1$ is 0.6 mm, then the radius of curvature $r_2$ may range from a low end of 0.2 mm to a high end of 1.8 mm, and vice versa.

Figure 7:
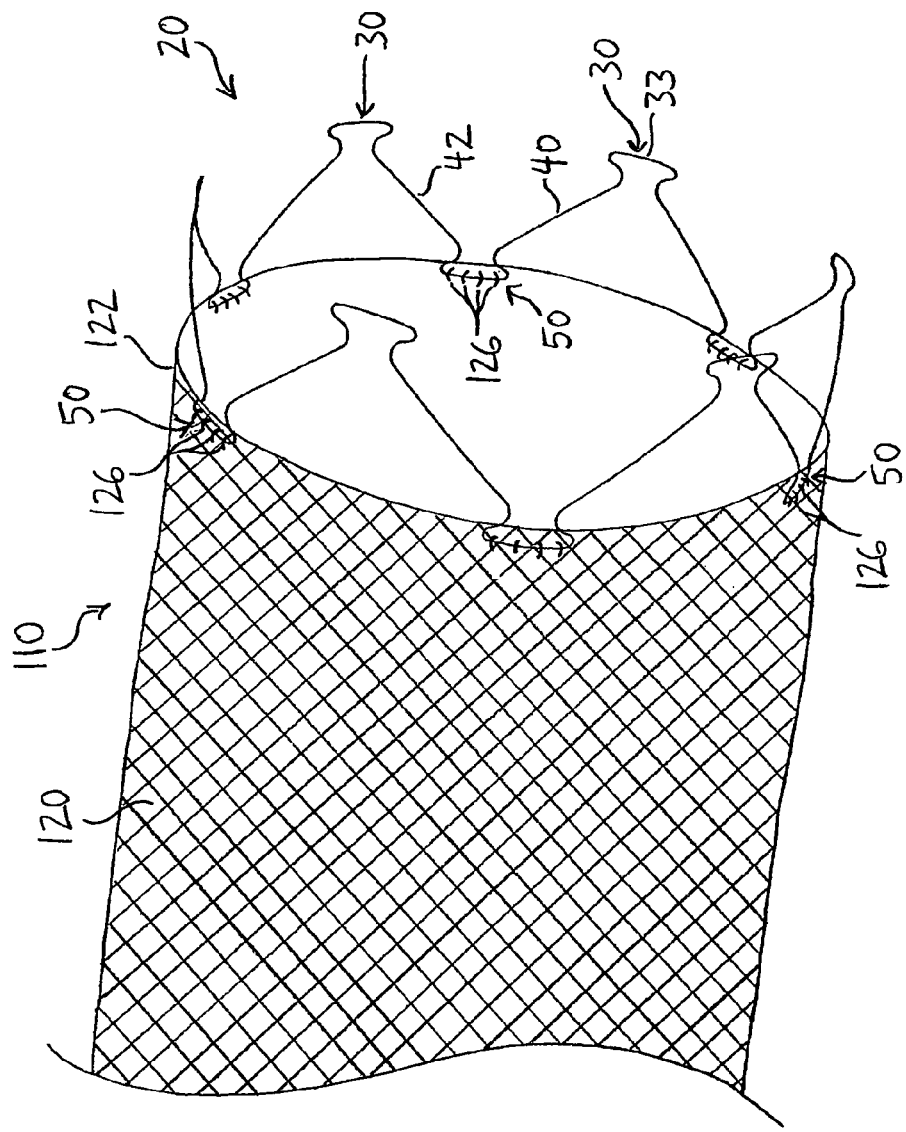
FIG. 7 is a perspective view of the stent of FIG. 1 coupled to an end region of a graft.

Advantageously, the relatively well-rounded curvature provided by the significantly increased radius of curvature $r_3$ of the third curved segments 33 and 53 allows the proximal and distal apices 30 and 50 to be less invasive upon a vessel wall and/or graft material when deployed. For example, if the stent 20 is used as an attachment stent for endovascular graft fixation and coupled to a distal end of a graft, as shown in FIG. 7 below, the relatively well-rounded curvature provided by the curved segments 53 of the distal apices 50 is less invasive on the graft material, while the relatively well-rounded curvature provided by the curved segments 33 of the distal apices 30 is less invasive on the vessel wall. Further, in this example, the well-rounded curvature provided by the curved segments 53 of the distal apices 50 facilitates suture attachment to the graft, as explained in further detail in FIG. 7 below.

The stent 20 may be manufactured from a super-elastic material. Solely by way of example, the super-elastic material may comprise a shape-memory alloy, such as a nickel titanium alloy (nitinol). Alternatively, the stent 20 may be made from other metals and alloys that allow the stent 20 to return to its preferred expanded configuration upon deployment, without inducing a permanent strain on the material due to compression. Such materials may include, but are not limited to, stainless steel, cobalt-chrome alloys, amorphous metals, tantalum, platinum, gold and titanium. The stent 20 also may be made from non-metallic materials, such as thermoplastics and other polymers.

Figure 4B:
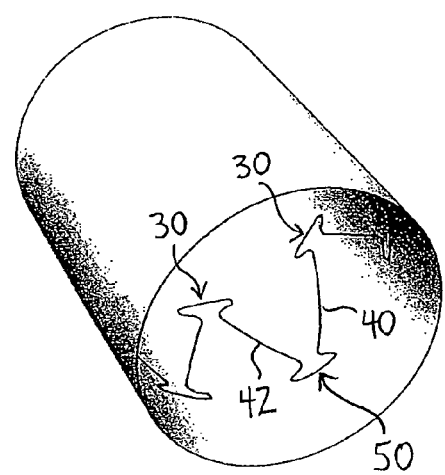
Figure 4C:
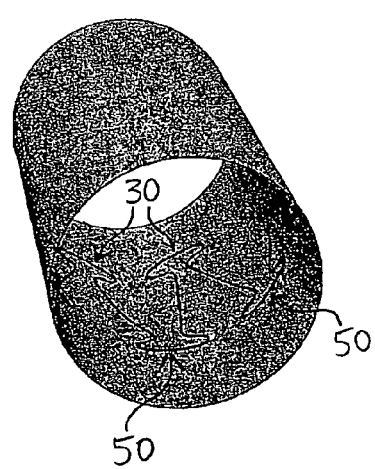
Figure 4D:
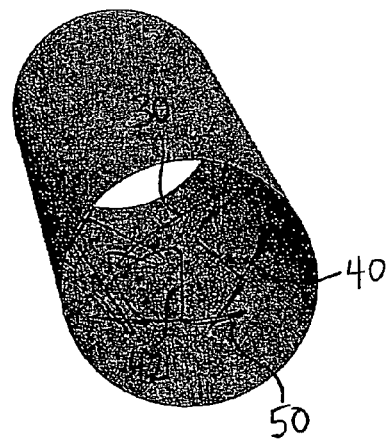

FIGS. 4A-4D show a computer simulation illustrating an exemplary compression sequence of the stent 20. In FIG. 4A, the stent 20 is shown in a 100% expanded state in a simulated vessel V. In FIGS. 4B-4D, the stent 20 is depicted in 50%, 75% and 100% crimped states, respectively. If the stent 20 is manufactured from nitinol, then when the stent is transformed between the expanded state of FIG. 4A to the fully compressed state of FIG. 4D, an overall strain imposed upon the stent should not exceed about 10-12%. If the strain imposed upon nitinol exceeds about 10-12%, then the stent compression may induce a strain on the material that may adversely impact fatigue or other characteristics of the stent. Based on analytical computer modeling that factors into account the above-mentioned characteristics of the stent 20, the strain imposed upon the stent will be about 6.0% in the fully compressed delivery state of FIG. 4D. Since the strain imposed will not exceed about 10-12% if manufactured from a super-elastic material, such as nitinol, the stent 20 therefore will return to its desired expanded shape upon removal from a delivery sheath. Thus the stent provides significantly larger radial force than existing z-stents while maintaining peak strain level in a safe range when compressed into the delivery system.

The design of the stent 20 provides several advantages over previously-known stents. First, as noted above, the significantly increased radius of curvature of the third curved portions 33 and 53 allows the proximal and distal apices 30 and 50 to be less invasive upon a vessel wall and/or graft material. Additionally, the significantly increased radius of curvature of the third curved segments 33 and 53 considerably improves conformance of the proximal and distal apices 30 and 50 to a vessel wall, thereby reducing endoleaks. Therefore, the stent 20 may be particularly suitable for uses including, but not limited to, sealing purposes.

Moreover, the design of the stent 20 provides a significantly increased radial force compared to previously-known stents. Specifically, analytical modeling shows that the relatively small radii of curvature $r_1$ and $r_2$, and their respective convex and concave shapes, allow the stent 20 to achieve an increased radial force of between 4.0 to 6.0N. It should be noted that the exact radial force is dependent, in part, upon variations in wire diameter. By contrast, a conventional Z-shaped stent may achieve a radial force of about 3.28N. Accordingly, the increased radial force of the stent 20 provides an enhanced engagement with a vessel wall which reduces endoleaks. Furthermore, the stent has a low profile which is desirable. The height h of the stent 20 may range from about 10.0 to about 12.0 mm, as noted above, compared to a height of about 14.0 mm for a conventional Z-shaped stent.

Figure 5:
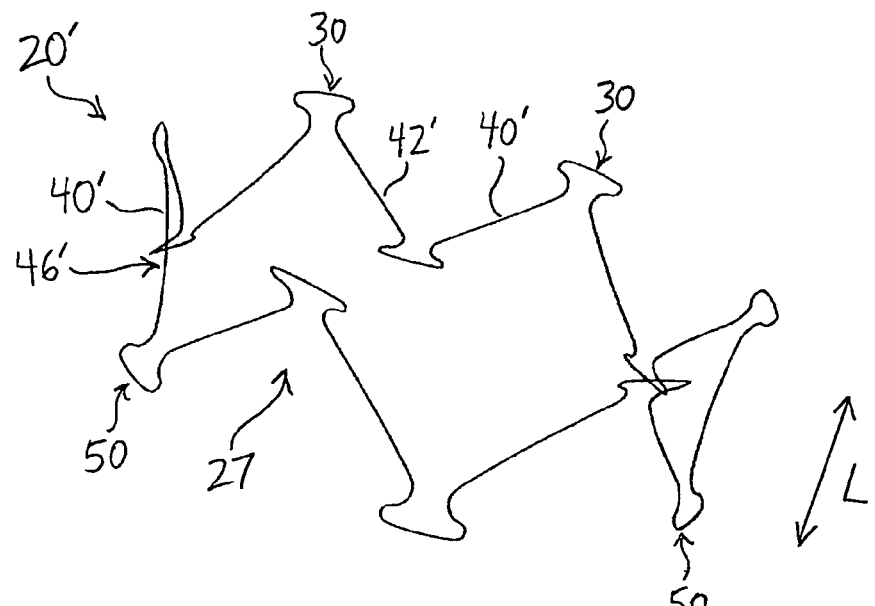
FIG. 5 is a perspective view of a second embodiment of a stent.
Figure 6:
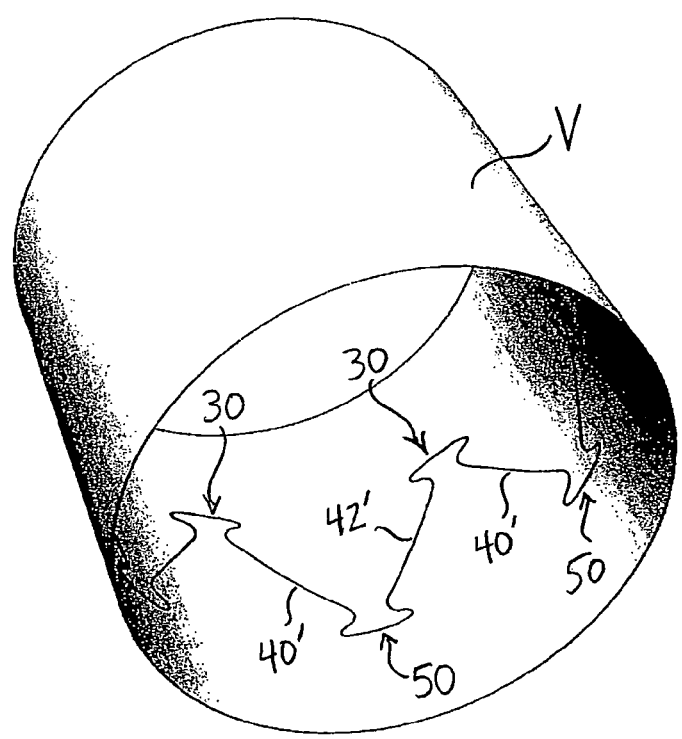
FIG. 6 is a perspective view of the stent of FIG. 5 disposed in a simulated vessel.

Referring now to FIGS. 5-6, an alternative stent 20' is shown. The alternative stent 20' is substantially identical to the stent 20 disclosed in FIGS. 1-4, with the exception that alternative first and second angled strut segments 40' and 42' each comprise a concave curvature, whereby the central region 46' is bowed radially inward towards the central lumen 27 in the expanded state. As shown in FIG. 5, by bowing the central region 46' radially inward, the proximal and distal apices are disposed further radially outward for engagement with the vessel wall. Accordingly, the proximal and distal apices 30 and 50 apply an increased force upon the vessel V, as depicted in FIG. 6, resulting in fewer endoleaks and which reduces or eliminates migration of the stent.

Additionally, analytical modeling of the stent 20' in a simulated vessel V indicates that the concave-shaped first and second angled strut segments 40' and 42', shown in FIGS. 5-6, help distribute stresses more evenly along the entirety of the stent 20', including at the proximal and distal apices 30 and 50. It will be appreciated that the desired amount of convex or concave curvature of the angled strut segments of the stent may be tailored depending on the particular application of the stent.

Referring now to FIG. 7, the stents 20 or 20', described above, may be coupled to a portion of graft material to form a stent-graft 110. In the embodiment of FIG. 7, the stents 20 or 20' may be used as an attachment stent for endovascular graft fixation. For example, the stent 20 may be coupled to a proximal end 122 of a graft 120. The graft 120 may overlap with an aneurysm to seal off fluid flow into the aneurysm, while the proximal end 22 of the stent 20 may extend in a proximal direction away from the graft 120, e.g., to engage a healthy portion of a vessel wall away from a diseased portion of the aneurysm.

During manufacture, the apices 50 at the distal end 24 of the stent 20 may be coupled to the graft 120, for example, using one or more sutures 126. In one example, multiple sutures are looped through the graft 120 around the third curved portions 53 of each distal apex 50. While four sutures are illustratively depicted, any number of sutures may be employed, ranging from one suture per apex to more than four sutures per apex.

Advantageously, since the third curved portions 53 comprise a significantly large radius of curvature, an increased suture attachment zone is provided, thereby allowing for the provision of a greater number of sutures and enhanced coupling between the stent 20 and the graft 120. Moreover, since the end regions of the distal apices 50 are not substantially pointed or acutely bent, a less invasive interface is provided between the stent 20 and the graft 120, thereby reducing the likelihood of abrading the graft material. Similarly, since the end regions of the proximal apices 30 are not substantially pointed or acutely bent in the deployed state, a less invasive interface is provided between the stent 20 and an inner surface of the vessel wall, thereby reducing the likelihood of damaging the vessel.

In other examples, the stent 20 may substantially overlap with the graft 120. For example, the stent 20 may be disposed substantially internal to the graft 120 and coupled to the graft 120 using sutures. In a further example, the stent 20 may be disposed substantially overlapping and external to the graft 120, and may be coupled to the graft using sutures.

Many different types of graft materials may be used for the graft 120. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues, including small intestine submucosa (SIS).

Moreover, the stent 20 may comprise at least one barb (not shown). The barb may be formed integrally with the stent 20, i.e., as part of a strut, e.g., by laser-cutting a barb and bending it into the desired configuration. Alternatively, one or more barbs may be coupled to the stent 20 by welding, or by using adhesive or mechanical techniques.

The bare stents 20 or 20', or the stent-graft 110 of FIG. 7, may be delivered into a vessel, duct, or other anatomical site using a suitable deployment system or introducer. An introducer, such as that described in PCT application WO98/53761, entitled "A Prosthesis and a Method and Means of Deploying a Prosthesis," which is incorporated herein by reference in its entirety, may be used to deploy the stent or stent-graft. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. Further, such delivery devices may be compact and may have a relatively uniform, low-diameter radial profile, allowing for atraumatic access and delivery.

The delivery and deployment device used to deploy the stent 20 or 20' and the stent-graft 110 may optionally include deployment control mechanisms. For example, a proximal control mechanism may releasably retain the proximal end of the stent-graft 110 and a distal control mechanism may releasably retain the distal end of the stent-graft 110. The proximal and distal control mechanisms may comprise one or more trigger wires that releasably couple the proximal and distal ends of the stent-graft 110 to the delivery catheter. Various prosthesis retention devices, configurations, and methods of use are disclosed in PCT application WO 98/53761, previously incorporated by reference. While the above-referenced PCT application described one system for delivering and deploying the stent 20 or 20' and the stent-graft 110, other suitable delivery and deployment systems may be used to deliver a stent or stent-graft manufactured in accordance with the embodiments and techniques described hereinabove.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

The invention claimed is:

1. An intravascular medical stent being formed from a single wire comprising a plurality of strut segments and apices coupling adjacent strut segments, each apex comprising multiple curved portions, wherein each of the curved portions comprises a radius of curvature, and wherein the radius of curvature of one of the curved portions is greater than each of the other radii of curvature of the apex,
wherein each apex comprises a first, second, third, fourth and fifth curved portion, wherein the first curved portion comprises a convex curvature relative to an interior space of the apex, the second, third and fourth curved portions each comprise a concave curvature relative to the interior space, and the fifth curved portion comprises a convex curvature relative to the interior space, and
wherein the third curved portion, which is configured to engage a vessel wall, comprises a radius of curvature that is at least 10 times greater than each of the other radii of curvature of the apex.

2. A stent as claimed in claim 1 wherein the radius of curvature of the third curved portions is from 25 to 40 times greater than each of the other radii of curvature of the apex.

3. A stent as claimed in claim 1, wherein the radius of curvature of the third curved portion is from 10 to 20 mm.

4. A stent as claimed in claim 1, wherein the first and fifth curved portions comprise substantially identical radii of curvature, and the second and fourth curved portions comprise substantially identical radii of curvature.

5. A stent as claimed in claim 1, wherein the first and second portions comprise substantially identical radii of curvature.

6. A stent as claimed in claim 1 wherein the radii of curvature of the first and second portions differ by a factor of 3.

7. A stent as claimed in claim 1 further comprising:
a series of proximal apices disposed at a proximal end of the stent;
a series of distal apices disposed at a distal end of the stent; and
first and second angled strut segments disposed between each proximal apex and each distal apex.

8. A stent as claimed in claim 7, wherein the first and second angled strut segments are disposed at an angle of about 70 to 110 degrees relative to each other in an expanded state.

9. A stent as claimed in claim 7, wherein a central region of at least one of the first and second angled strut segments comprises a convex curvature, such that the central region is flared radially outward with respect to a central lumen of the stent in the expanded state.

10. A stent as claimed in claim 7, wherein a central region of least one of the first and second angled strut segments comprises a concave curvature, such that the central region is bowed radially inward with respect to a central lumen of the stent in the expanded state.

11. A stent as claimed in claim 7, wherein at least one of the first and second angled strut segments is substantially straight.

12. A stent as claimed in claim 7, wherein each of the proximal apices are circumferentially offset from each of the distal apices in an expanded state.

13. A stent as claimed in claim 7, wherein the longitudinal distance between an end of a proximal apex and an end of a distal apex ranges from about 10 mm to about 20 mm.

14. A stent as claimed in claim 7, wherein the stent is coupled to at least a portion of a graft, where at least one distal apex of the stent is coupled to the graft using one or more sutures.

15. An intravascular medical stent being formed from a single wire comprising a plurality of strut segments and apices coupling adjacent strut segments, each apex comprising multiple curved portions, wherein each of the curved portions comprises a radius of curvature, and wherein the radius of curvature of one of the curved portions is greater than each of the other radii of curvature of the apex;
a series of proximal apices disposed at a proximal end of the stent;
a series of distal apices disposed at a distal end of the stent; and
first and second angled strut segments disposed between each proximal apex and each distal apex, wherein at least one of the proximal and distal apices comprises a first, second, third, fourth and fifth curved portion, and wherein a first angled strut segment transitions into the first curved portion of the apex, and the first curved portion transitions into the second, third, fourth and fifth curved portions of the apex, respectively, and the fifth curved portion of the apex transitions into a second angled strut segment.

16. A stent as claimed in claim 15 wherein the radius of curvature of the third curved portion is at least 10 times greater than each of the other radii of curvature of the apex.

17. A stent as claimed in claim 15 wherein the radius of curvature of the third curved portion is from 25 to 40 times greater than each of the other radii of curvature of the apex.

18. A stent as claimed in claim 15, wherein the stent is coupled to at least a portion of a graft, where at least one distal apex of the stent is coupled to the graft using one or more sutures.

19. A stent as claimed in claim 15, wherein a central region of at least one of the first and second angled strut segments comprises a convex curvature, such that the central region is flared radially outward with respect to a central lumen of the stent in the expanded state.

20. A stent as claimed in claim 15, wherein a central region of least one of the first and second angled strut segments comprises a concave curvature, such that the central region is bowed radially inward with respect to a central lumen of the stent in the expanded state.

* * * * *